| United States Patent [19] | [11] | Patent Number: | 4,466,963 |
|---|---|---|---|
| Cavalla et al. | [45] | Date of Patent: | Aug. 21, 1984 |

[54] PHARMACEUTICAL COMPOSITIONS

[75] Inventors: John F. Cavalla, Isleworth; Roger J. Stephens, Marlow, both of England

[73] Assignee: John Wyeth & Brother Limited, Maidenhead, England

[21] Appl. No.: 510,868

[22] Filed: Jul. 5, 1983

[30] Foreign Application Priority Data

Jul. 8, 1982 [GB] United Kingdom ................ 8219837

[51] Int. Cl.³ ...................... A61K 31/19; A61K 31/33
[52] U.S. Cl. .................................... 424/244; 424/317
[58] Field of Search ................................ 424/244, 317

[56] References Cited

FOREIGN PATENT DOCUMENTS

| 0068838 | 6/1982 | European Pat. Off. | ............... 31/485 |
| 0971700 | 1/1962 | United Kingdom . | |
| 1285025 | 8/1969 | United Kingdom | ..................... 41/2 |

OTHER PUBLICATIONS

Chem. Abst., vol. 96-149162u, (1982).
Copeman, Annals of the Rheumatic Diseases, vol. XXVIII, (1969), pp. 513-516.

*Primary Examiner*—Stanley J. Friedman
*Attorney, Agent, or Firm*—Richard K. Jackson

[57] ABSTRACT

Pharmaceutical compositions containing meptazinol or a pharmaceutically acceptable acid addition salt thereof and ibuprofen or a pharmaceutically acceptable salt thereof are useful in treating pain in mammals.

4 Claims, No Drawings

PHARMACEUTICAL COMPOSITIONS

This invention relates to pharmaceutical compositions possessing analgesic activity.

Meptazinol is a synthetic non-narcotic analgesic agent. The compound is m-(3-ethylhexahydro-1-methyl[1H]azepin-3-yl) phenol. The preparation of meptazinol and its pharmaceutically acceptable acid addition salts are described in, for example, U.K. Patent Specification No. 1,285,025. Ibuprofen is an anti-inflammatory agent and has also been recommended for the relief of pain in man and animals. The compound is 2-(4-isobutylphenyl)propionic acid and it is described, together with its pharmaceutically acceptable salts, in, for example, U.K. Patent Specification No. 971,700.

We have found that the analgesic or antinociceptive activity possessed by meptazinol is unexpectedly potentiated by the co-administration of ibuprofen. Thus a combination of meptazinol or a pharmaceutically accepatable acid addition salt and ibuprofen or a pharmaceutically acceptable salt thereof possesses properties which are surprisingly greater than the additive properties of the individual components of the combination.

Accordingly, in one aspect, the invention relates to a process for treating pain in mammals, particularly humans, by administering to the mammals, preferably by the oral route and preferably simultaneously, meptazinol or a pharmaceutically acceptable acid addition salt thereof and ibuprofen or a pharmaceutically acceptable salt thereof.

The present invention particularly provides a pharmaceutical composition comprising a pharmaceutically acceptable carrier and an analgesically effective amount of (a) an analgesic agent selected from the group consisting of meptazinol and pharmaceutically acceptable acid addition salts thereof and (b) ibuprofen or a pharmaceutically acceptable salt thereof.

The surprising efficacy of the novel compositions of the invention has been demonstrated in various pharmacological procedures. For example in one method used to measure the antinociceptive effects of meptazinol, ibuprofen and combinations of the two drugs, groups of 9 mice were given 0.025 ml of 2% carrageenin (in saline) sc into the plantar surface of both hind feet 3.0 hours before treatment. The latency to a distinct response following placement of the mice on a brass hot-plate (55° C.) was measured immediately prior to dosing with vehicle (0.5% hydroxypropyl-methylcellulose in water) or with drug.

The antinociceptive response at each recording time (t) was defined as the reaction time of the mouse at time t minus the reaction time at t=0 (immediately prior to dosing).

The results after dosing with vehicle, ibuprofen (240 mg/kg), meptazinol (40 mg/kg) and a combination of ibuprofen (240 mg/kg)+meptazinol (40 mg/kg) are given in Table 1 below:

TABLE 1

Effect of a combination of ibuprofen (240 mg/kg) and meptazinol (40 mg/kg) po on the hot-plate response latency of mice pretreated with carrageenin

| Treatment (doses, mg/kg · po) | Latency (sec) pre-dose control | Increase in latency (sec) cf. pre-dose control at following times (min) post dosing. (SEM) | | |
|---|---|---|---|---|
| | | 30 | 60 | 90 |
| Vehicle | 6.33 (0.41) | 0.51 (0.26) | 0.50 (0.11) | 0.58 (0.91) |
| Ibuprofen (240) | 7.16 (0.47) | −0.72* (0.32) | −1.56* (0.20) | −1.30 (0.69) |
| Meptazinol (40) | 6.41 (0.62) | 4.76* (1.48) | 3.00* (0.72) | 1.76 (0.95) |
| Ibuprofen (240) + Meptazinol (40) | 5.82 (0.55) | 11.77$^x$ (2.15) | 8.09 (2.73) | 7.94$^x$ (1.88) |

*$p < .02$ cf vehicle treated controls
$^x p < .02$ cf meptazinol alone

In this experiment ibuprofen at 240 mg/kg did not produce any antinociceptive response when administered alone, the reaction time of mice given ibuprofen alone being shorter than that of the controls. However, the amplitude of the antinociceptive response to 40 mg/kg meptazinol was more than doubled (at 30, 60 and 90 minutes post treatment) when the meptazinol (40 mg/kg) was administered with ibuprofen (240 mg/kg).

A similar trend of potentiation was found when the antinociceptive responses produced by 20 mg/kg and 40 mg/kg meptazinol were compared with the responses produced by 120 mg/kg ibuprofen administered alone and with the meptazinol.

In a further experiment groups of 10 normal mice were given meptazinol (40 mg/kg), ibuprofen (240 mg/kg), a mixture containing these doses of meptazinol and ibuprofen or the requisite volume of vehicle po immediately after measuring the latency to a distinct tail flick (following tail immersion in water at 50° C.). Tail flick latencies were measured again at 30 min intervals post dosing. As the mean pre-dose latencies of mice subjected to the tail immersion procedure were so similar to one another comparisons of the actual latencies at each recording time were made (Student's "t" test).

The results are given in Table 2 below:

TABLE 2

Effects of meptazinol (40 mg/kg), ibuprofen (240 mg/kg) and a combination of the two drugs on the tail flick latencies of mice (tail immersion in water at 50% C)

| Treatment (doses, mg/kg po) | Latency to a distinct tail flick (sec) at following times (min) post dosing (SEM) | | | |
|---|---|---|---|---|
| | 0 | 30 | 60 | 90 |
| Vehicle | 3.44 (0.52) | 3.68 (0.49) | 4.19 (0.51) | 3.25 (0.25) |
| Ibuprofen (240) | 3.43 (0.49) | 2.75 (0.28) | 3.04 (0.29) | 3.94 (0.47) |
| Meptazinol (80) | 3.54 (0.40) | 6.95*** (0.69) | 6.75** (0.72) | 6.37*** (0.35) |
| Meptazinol (40) | 3.43 (0.33) | 4.24 (0.47) | 4.85 (0.49) | 4.80 (0.93) |
| meptazinol (40)+ ibuprofen (240) | 3.72 (0.37) | 6.90$^x$ (1.12) | 7.42$^{xx}$ (0.47) | 6.42 (0.65) |

**$p < .01$
***$p < .0001$ cf vehicle control
$^x p < .05$
$^{xx} p < .01$ cf meptazinol alone In this experiment, 40 mg/kg meptazinol alone did induce a significant antinociceptive response but, in combination with 240 mg/kg ibuprofen, the response to this dose of meptazinol was almost identical to that following the oral administration of 80 mg/kg alone. Also ibuprofen alone did not significantly affect the tail flick latency (although the mean latency of the group given ibuprofen was smaller than that of the controls at all time points).

In a further experiment the brain concentration of meptazinol was measured after administration of meptazinol alone or a combination of ibuprofen and meptazinol. Groups of mice were given meptazinol (40 mg/kg) alone or meptazinol+ibuprofen (40+240 mg/kg) po containing 25 μCi/mouse of $^3$H meptazinol. Six mice from each group were decapitated at 30 min intervals after dosing. The brain of each animal was removed and after the removal of the cerebellum, pons and medulla the remainder was homogenised in 10 ml ice cold Tris buffer. This was immediately centrifuged at 20,000 rpm for 5 min then a single 1 ml aliquot of the supernatant was taken for counting.

In all experiments the counts obtained from samples derived from mice treated with meptazinol alone were compared (Students 't' test) with those obtained from mice that had received meptazinol plus the ibuprofen.

It was found that the concentration of tritium in the brain of mice dosed with 40 mg/kg H-meptazinol was approximately half that in the brain of mice given the same dose of meptazinol with 240 mg/kg ibuprofen (at 30, 60 and 90 min post dosing); see Table 3 below. As previous studies have shown that virtually all of the tritium in the brain of rats given $^3$H meptazinol is in the form of meptazinol the results indicate that the co-administration of ibuprofen caused a significant enhancement of the brain concentration of meptazinol compared to that of mice given meptazinol alone. This effect closely parallels the enhancement of the antinociceptive effect of meptazinol by ibuprofen indicated by the other experiments reported above.

TABLE 3

Effects of co-administration of ibuprofen with meptazinol on the brain concentration of meptazinol

| Treatment (doses, mg/kg po) | Counts × 1000/min/g brain at following times (min) post treatment | | | |
|---|---|---|---|---|
| | 30 | 60 | 90 | 120 |
| Meptazinol (40) | 18.4 | 12.0 | 7.4 | 4.7 |
| | (2.2) | (1.4) | (0.8) | (0.8) |
| Meptazinol + ibuprofen (40 + 240) | 45.4** | 23.5 | 15.6* | 18.6** |
| | (6.9) | (10.1) | (2.8) | (4.3) |

*$p < .05$;
**$p < .01$ cf meptazinol alone

Compositions of the present invention have been found, in pharmacological tests, to have a further advantage. It is well known that non-steroidal anti-inflammatory agents such as ibuprofen induce gastric damage. Experiments were performed in which the degree of gastric erosion in rats was assessed four hours after the oral administration of ibuprofen (120 mg/kg) with or without the co-administration of 30-90 mg/kg meptazinol. There was a consistent tendency (although not statistically significant at the $p<0.05$ level) for the severity of the erosions induced by a single dose of ibuprofen to be less marked in rats co-administered 30-90 mg/kg meptazinol than in those given ibuprofen alone. This protective effect of meptazinol was more marked and statistically significant ($p<0.05$) in rats given five daily doses of ibuprofen (120 mg/kg) plus meptazinol (90 mg/kg) than in those given a single dose of the mixture.

The novel compositions of the present invention may be used in alleviating pain in mammals, particularly humans. Thus the invention also provides a method of alleviating pain in mammals which comprises administering to a mammal in need thereof a composition according to the invention. The compositions may be used in alleviating pain, and possibly inflammation, associated with arthritic diseases, e.g. rheumatoid arthritis, Still's disease and osteoarthritis and various types of non-specific inflammatory or rheumatic conditions. The compositions may also be useful in alleviating pain in other conditions which are not primarily associated with arthritic diseases, for example pain associated with musculo-skeletal injury, dental and post-operative pain and the like.

Preferably the novel compositions of the invention are in unit dosage form, e.g. as tablets or capsules. In such form the composition is sub-divided in unit doses containing appropriate quantities of the active ingredients (a) and (b). The unit dosage form can be, for example, a capsule or tablet itself or it can be an appropriate number of such compositions in package form. The quantity of the active ingredients in the unit dosage forms may be varied or adjusted according to the particular need of the patient or the condition being treated. Generally the compositions contain a potentiating amount of ibuprofen or pharmaceutically acceptable salt thereof i.e. an amount sufficient to potentiate the analgesic effect of the meptazinol or a pharmaceutically acceptable acid addition salt thereof. For example, one part by weight of meptazinol or a pharmaceutically acceptable acid addition salt thereof may be administered with at least 3 (e.g. 3 to 6, particularly 4) parts by weight ibuprofen or a pharmaceutically acceptable acid addition salt thereof. Unit dosages for alleviation of pain in humans may, for example, contain from about 50 to 300 mg (preferably 100 to 200 mg) of meptazinol or a pharmaceutically acceptable salt thereof and 100 to 800 mg (preferably 200 to 400 mg) of ibuprofen or a salt thereof.

The compositions of the present invention may be prepared by bringing the active ingredients into association with (e.g. by mixing with) the pharmaceutically acceptable carrier.

Any suitable carrier known in the art can be used to prepare the pharmaceutical composition of the present invention. In such a composition, the carrier is generally a solid or liquid, or a mixture of a solid and a liquid.

Solid form compositions include powders, granules, tablets, capsules (e.g. hard and soft gelatin capsules), suppositories and pessaries. A solid carrier can be, for example, one or more substances which may also act as flavouring agents, lubricants, solubilisers, suspending agents, fillers, glidants, compression aids, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g. from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of the active ingredient with encapsulating material as carrier to give a capsule in which the active ingredients (with or without other carriers) is surrounded by the carrier, which is thus in association with it. Similarly cachets are included.

Liquid form compositions include, for example, solutions, suspensions, emulsions, syrups, elixirs and pressurised compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilisers, emulsifiers, buffers. preservatives, sweeteners, flavouring agents, suspending agents, thickening agents, colours, viscosity regulators, stabilisers or osmo-regulators. Suitable examples of liquid carriers for oral administration include water (particularly containing additives as above e.g. cellulose derivatives, preferably sodium carboxymethyl cellulose solution), alcohols (including monohydric alcohols and polyhydric alcohols e.g. glycerol and glycols) and their derivatives, and oils (e.g. fractionated coconut oil and arachis oil).

Preferably the compositions of the present invention are administered orally either in liquid or solid composition form.

The following Examples illustrate the invention

Examples 1 to 5

Tablets of the following compositions are made by mixing batches of the ingredients and compressing to forms tablets

|  | Example 1 mg/tablet | Example 2 mg/tablet |
|---|---|---|
| Meptazinol hydrochloride | 57.8 | 115.6 |
| Ibuprofen | 200.0 | 400.0 |
| Avicel pH 101 (microcrystalline cellulose) | 80.0 | 160.0 |
| Lactose hydrous BP | 40.2 | 80.4 |
| Explotab (sodium starch glycolate USP) | 20.0 | 40.0 |
| Magnesium Stearate B.P. | 2.0 | 4.0 |
|  | 400.0 | 800.0 |

Example 3

|  | mg/tablet |
|---|---|
| Meptazinol hydrochloride | 231.2 |
| Ibuprofen | 300.0 |
| Avicel pH 101 | 124.4 |
| Anhydrous lactose USP | 124.4 |
| Amberlite IRP 88 | 16.0 |
| Magnesium stearate BP | 4.0 |
|  | 800.0 |

Example 4

|  | mg/tablet |
|---|---|
| Meptazinol hydrochloride | 115.6 |
| Ibuprofen | 300.0 |
| Avicel pH 101 | 75.4 |
| Anhydrous lactose USP | 100.0 |
| Amberlite IRP 88 | 6.0 |
| Magnesium Stearate BP. | 3.0 |
|  | 600.0 |

Example 5

|  | mg/tablet |
|---|---|
| Meptazinol hydrochloride | 57.8 |
| Ibuprofen | 400.0 |
| Avicel pH 101 | 138.7 |
| Anhydrous Lactose U.S.P. | 100.0 |
| Explotab | 40.0 |
| Talc BP | 10.0 |
| Magnesium stearate BP | 3.5 |
|  | 750.0 |

Examples 6 to 8

Capsules of the following compositions are made by mixing together batches of the following ingredients and filling hard gelatine capsules with the mixture.

|  | Example 6 mg/capsule | Example 7 mg/capsule |
|---|---|---|
| Meptazinol hydrochloride | 57.8 | 115.6 |
| Ibuprofen | 200.0 | 400.0 |
| Lactose hydrous B.P. | 61.2 | 52.4 |
| Maize starch dried B.P. | 20.0 | 20.0 |
| Talc B.P. | 10.0 | 10.0 |
| Magnesium stearate B.P. | 1.0 | 2.0 |
|  | 350.00 | 600.0 |

Example 8

|  | mg/capsule |
|---|---|
| Meptazinol hydrochloride | 231.2 |
| Ibuprofen | 200.0 |
| Lactose hydrous B.P. | 52.8 |
| Maize starch dried B.P. | 50.0 |
| Talc B.P. | 15.0 |
| Magnesium stearate B.P. | 1.0 |
|  | 550.0 |

Example 9

(a) Tablets of the following compositions were prepared:

|  | mg/tablet |
|---|---|
| Part I |  |
| Meptazinol HCl | 115.60 |
| Ibuprofen BP | 400.00 |
| Avicel PH 101 | 120.00 |
| Lactose BP | 104.40 |
| Explotab | 8.50 |
| Water q.s. |  |
| Part II |  |
| Avicel PH 101 | 76.00 |
| Explotab | 8.50 |
| Kollidon CL (crosslinked polyvinylpyrrolidone) | 4.25 |
| Syloid 244 (silica gel) | 4.25 |
|  | 850.00 |

The Part I ingredients were wet massed with water and passed through a No. 8 screen. After drying in an oven the granules were passed through a No. 16 screen and blended with the Part II ingredients. The mixture was compressed and the tablets film coated with a composition comprising-

| | |
|---|---|
| Polyethylene glycol 400 NF | 1.0 |
| Hydropropyl methylcellulose USP | 6.0 |
| Colour | q.s. |
| Water | to 100 g. |

(b) In alternative tablets the lactose in Part I was replaced by a further 104.40 mg/tablet of Avicel PH101

Example 10

Two layered tablets were prepared from the following ingredients:

| Ingredients | mg/tablet |
|---|---|
| Layer I | |
| Part I | |
| Meptazinol HCl | 115.60 |
| Avicel PH 101 | 37.20 |
| Water q.s. | |
| Part II | |
| Avicel PH 101 | 37.20 |
| Explotab | 9.00 |
| Magnesium Stearate | 1.00 |
| | 200.0 |
| Layer II | |
| Part I | |
| Ibuprofen BP | 400.0 |
| Avicel PH 101 | 150.0 |
| Explotab | 15.0 |
| Water q.s. | |
| Part II | |
| Avicel PH 101 | 40.50 |
| Explotab | 6.50 |
| Kollidon CL | 6.50 |
| Magnesium Stearate BP | 3.25 |
| Syloid 244 | 3.25 |
| | 625.00 |

The Part I ingredients for each layer were mixed and wet massed with water. The wet mass was passed through a No. 8 screen and dried. The dried granules were passed through a No. 16 screen. The resulting granules from each layer were then blended with the corresponding Part II ingredients and the two layers were compressed using a two layer press.

We claim:

1. A process for treating pain in a mammal which comprises administering to the mammal one part by weight of meptazinol or a pharmaceutically acceptable acid addition salt thereof and about 3 to 6 parts by weight of ibuprofen or a pharmaceutically acceptable salt thereof.

2. A pharmaceutical composition comprising a pharmaceutically acceptable carrier and an analgesically effective amount of
   (a) one part by weight of an analgesic agent selected from the group consisting of meptazinol and pharmaceutically acceptable acid addition salts thereof, and
   (b) about 3 to 6 parts by weight of ibuprofen or a pharmaceutically acceptable salt thereof.

3. A process for treating pain in a mammal which comprises administering to the mammal a dosage unit comprising about 50 to 300 mg of meptazinol or a pharmaceutically acceptable acid addition salt thereof and about 100 to 800 mg of ibuprofen or a pharmaceutically acceptable salt thereof.

4. A pharmaceutical composition in unit dosage form comprising a pharmaceutically acceptable carrier and
   (a) about 50 to 300 mg of an analgesic agent selected from the group consisting of meptazinol and pharmaceutically acceptable acid addition salts thereof, and
   (b) about 100 to 800 mg of ibuprofen or a pharmaceutically acceptable salt thereof.

* * * * *